United States Patent [19]
Nuttle

[11] Patent Number: 5,121,708
[45] Date of Patent: Jun. 16, 1992

[54] HYDROCULTURE CROP PRODUCTION SYSTEM

[76] Inventor: David A. Nuttle, P.O. Box 201, Sperryville, Va. 22740

[21] Appl. No.: 655,334

[22] Filed: Feb. 14, 1991

[51] Int. Cl.⁵ .................... A01K 63/04; A01K 63/06
[52] U.S. Cl. ............................................ 119/3; 47/1.4
[58] Field of Search ................. 119/2, 3, 4, 5; 47/1.4

[56] References Cited

U.S. PATENT DOCUMENTS

| | | | |
|---|---|---|---|
| 4,065,875 | 1/1978 | Sina | 119/2 |
| 4,137,868 | 2/1979 | Pryor | 119/2 |
| 4,169,050 | 9/1979 | Serfling | 119/3 |
| 5,036,618 | 8/1991 | Mori | 119/3 |

FOREIGN PATENT DOCUMENTS

| | | | |
|---|---|---|---|
| 2332396 | 1/1975 | Fed. Rep. of Germany | 119/3 |
| 2809493 | 9/1979 | Fed. Rep. of Germany | 119/3 |
| 83/03333 | 10/1983 | PCT Int'l Appl. | 119/3 |
| 789082 | 12/1980 | U.S.S.R. | 119/3 |

*Primary Examiner*—John G. Weiss
*Attorney, Agent, or Firm*—John G. Mills

[57] ABSTRACT

This invention is a system for raising land and aquatic, plant and animal crops in a symbiotic-type polyculture using organic/sustainable methods of agronomy, animal husbandry, aquaculture, and hydroponics whereby yields are optimized while reducing production costs, conserving resources, and protecting the environment. Year-round production is also achieved by providing a canopy means along with additional environmental control and supplemental systems that increase yields in temperature zones normally having ambient temperature fluctuations too great to sustain production for more than a few months per year. Any number of cropping combinations are possible, but as an example, this system would establish a beneficial symbiotic-type production link between poultry, microalgae, fish and aquatic animals that consume algae, and vegetables or other land crops.

20 Claims, 8 Drawing Sheets

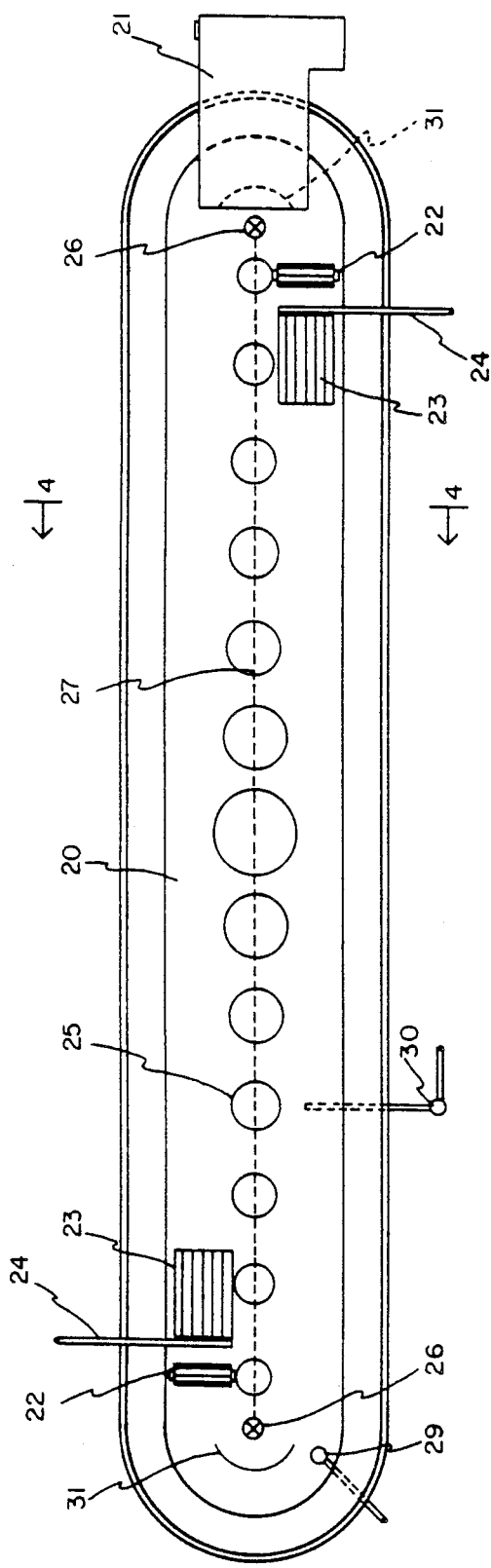
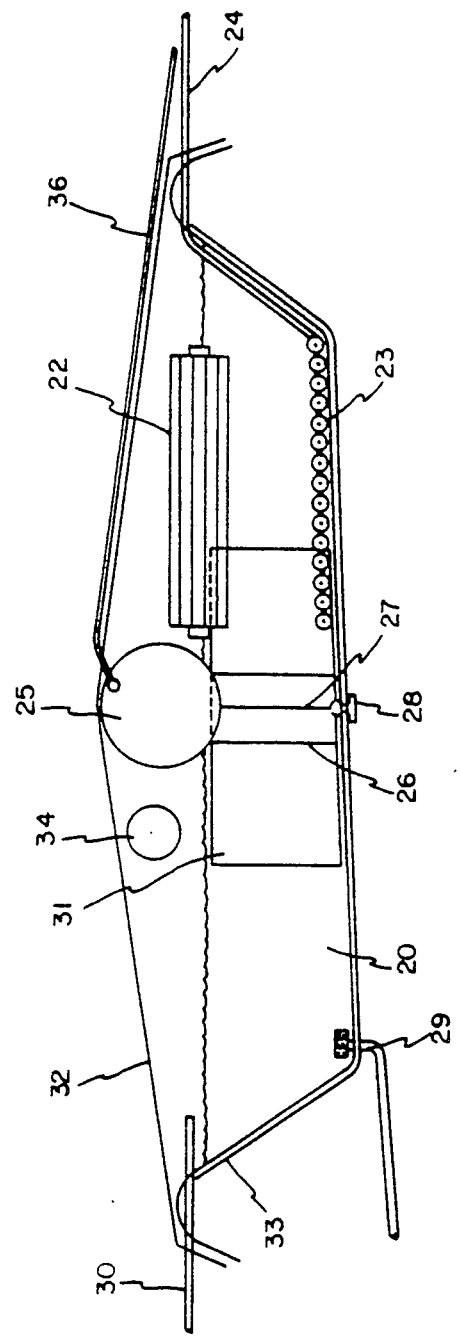
FIG. 3
FIG. 4

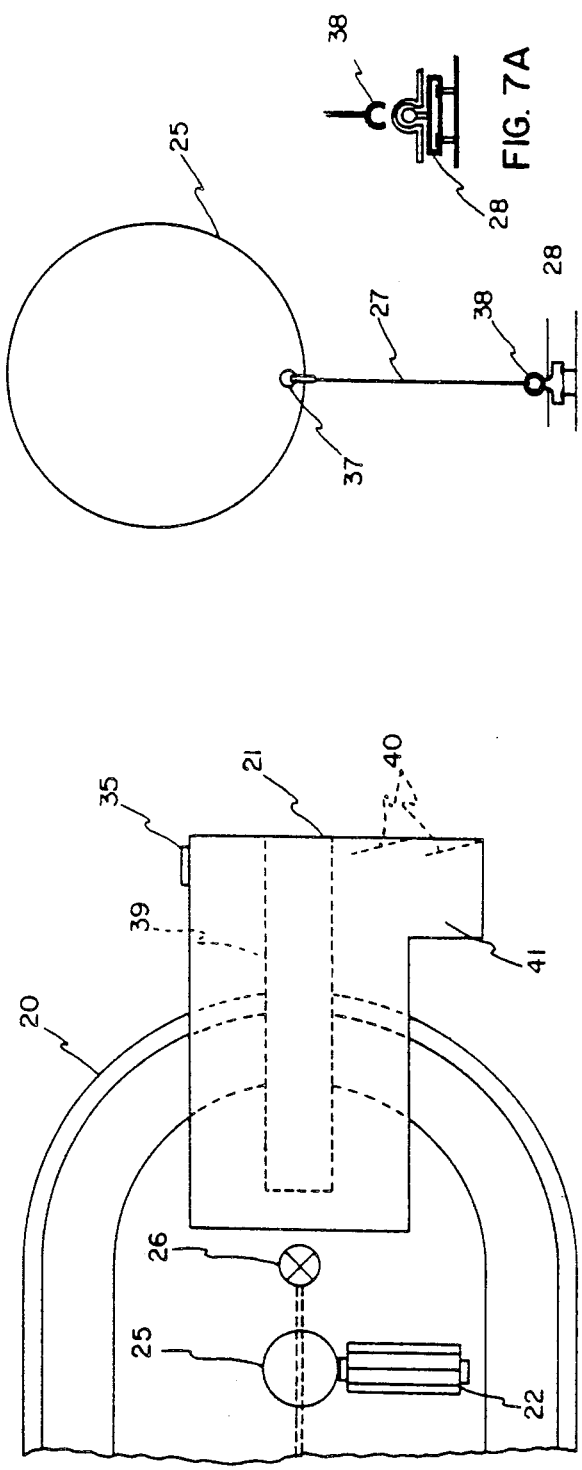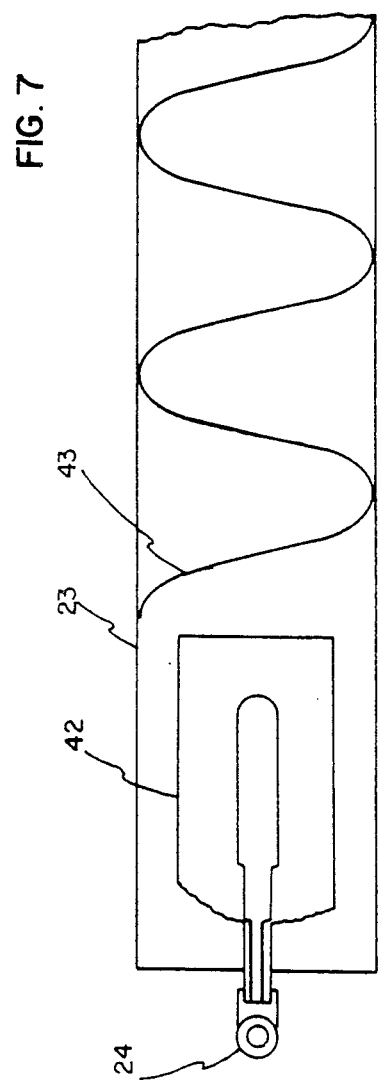
FIG. 7A
FIG. 7
FIG. 6
FIG. 5

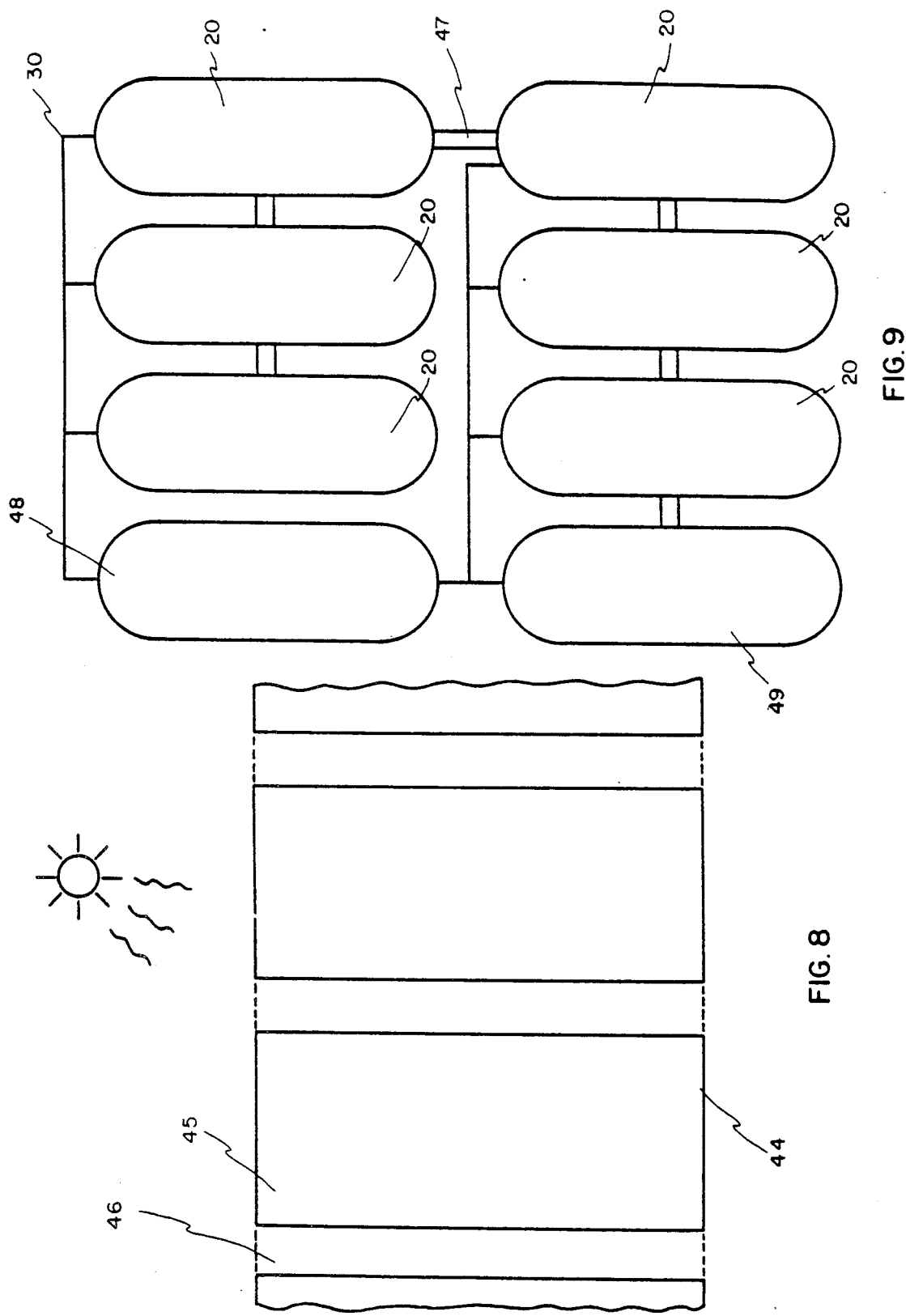

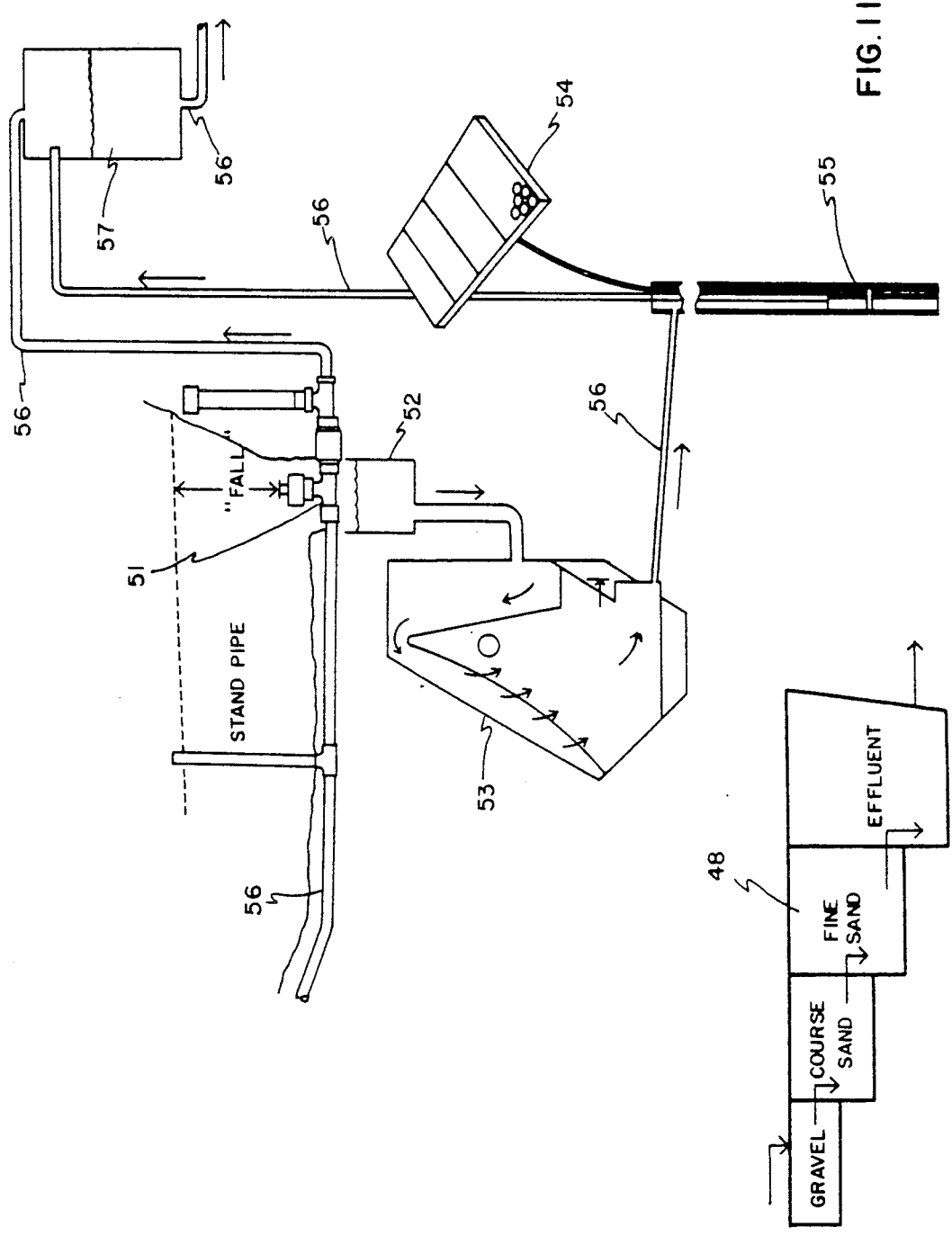

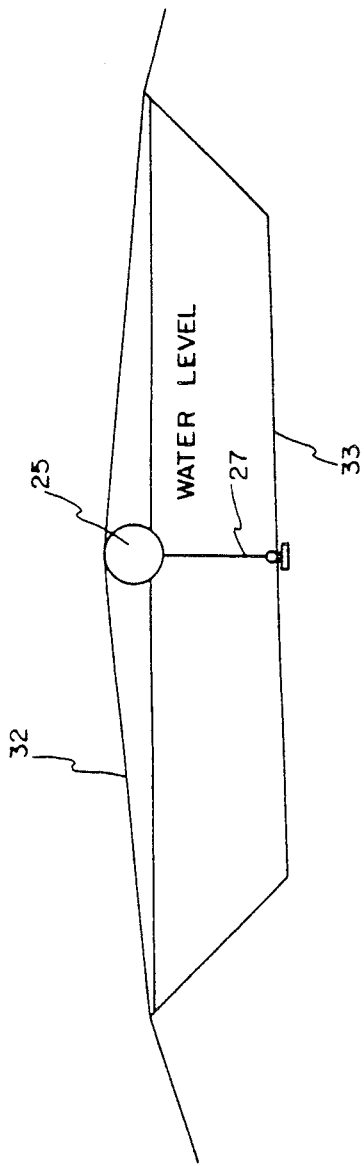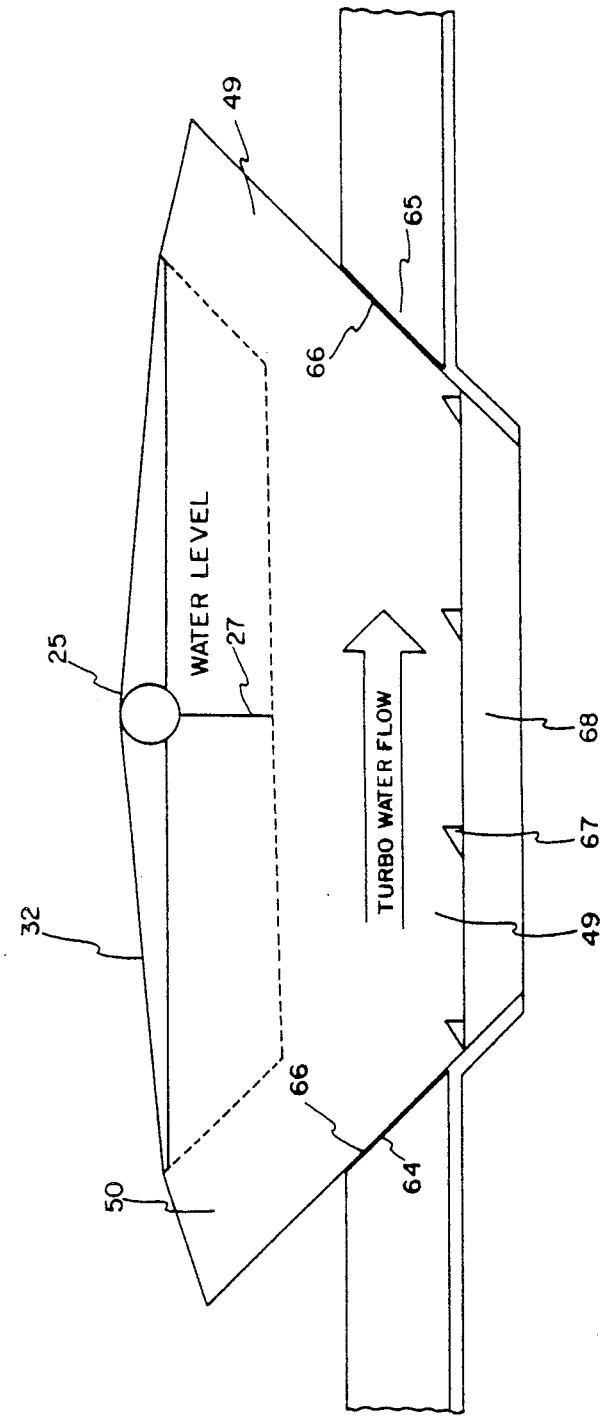

HYDROCULTURE CROP PRODUCTION SYSTEM

FIELD OF INVENTION

This relates to the organic/sustainable production of land and aquatic, plant and animal species, and more particularly to raising a wide array of land and aquatic crops in a polyculture wherein plants and animals help to sustain and support the growth of other plants and animals in an environment that is controlled to facilitate year-round production under a variety of conditions not usually favorable for plant or animal growth.

BACKGROUND OF THE INVENTION

The world has limited resources but the world's population, now over 5 billion, continues to increase. A habit of inefficient utilization of resources, and the practice of environmental pollution, must both be overcome while also overcoming increasingly critical food shortages. A new era of organic/sustainable agriculture is needed wherein air, land, and water are protected from the chemical and other pollution of the recent past while crop yields are increased With fewer resources and less cost.

A 5,000 year old Chinese polyculture method of crop production employed organic/sustainable agricultural methods. Ducks, grown for meat and eggs, were grown on rice paddies feeding on a portion of rice plants. The duck feces provided fertilizer for rice and nutrients for microalgae. A fish crop such as Tilapea was produced on the algae in the paddies, and any mature algae that died, plus fish feces, also provided fertilizer for the rice crop. Yields of each of these plant and animal crops benefited because of a symbiotic-type relationship that increased the yields of each. Pest control was accomplished by natural and organic means so that no pollution of the environment occurred. As an example, extracts from Neem (*Azadirachta indica*) tree seeds were used as a natural pesticide that controlled 131 species of harmful insects.

To help fully understand this invention, the background on several related agricultural systems is reviewed below.

1) Agronomy is the science of growing land crops in soils, and it involves selective breeding of plants and the management of soils to increase crop production. Todays soil management problems include wind and water erosion, maintenance of soil fertility, and several types of chemical pollution, and other problems. The latter includes acid rain, improper waste disposal, chemical pesticide build-up, water pollution, the "greenhouse effect," desertification, deforestation, urbanization and many factors now reducing land crop yields.

2) Hydroponics is the science of growing land crops without soil. Plants are typically suspended with their roots in water or in watered coarse sand or gravel. Chemical nutrients are added to the water to replace those nutrients normally provided by the soil and/or fertilizers. Artificial light and heat may be used for plants grown indoors by hydroponic means. Usual nutrients added to each 1,000 gallons of water are 2.6 kilograms of potassium nitrate, 0.5 kilograms of ammonium sulfate, 2 kilograms of magnesium sulfate, 1.1 kilograms of monocalcium sulfate, and 2.3 kilograms of calcium sulfate. One gallon (3.8 liters) of water containing 28 grams of manganous sulfate and 3 to 5 drops of sulfuric acid is usually added to the above 1,000 gallon mixture once a month. In addition, 113 grams of ferrous sulfate in 1 gallon of water is usually added once a week to the above 1,000 gallon mix. In brief, it takes a person skilled in the knowledge of plant nutrients, and one who is also skilled in the study of plant foliage nutrient deficiency symptoms, to manage a successful hydroponic operation.

3) Animal husbandry is the science of producing livestock such as cattle, hogs, horses, poultry, and sheep for the products they furnish or the services they provide. Practices of this science include the selected breeding and feeding of livestock, providing necessary shelter, and the prevention and/or control of animal diseases. Meat products from these land animals are not as popular as they once were. Fats from animal meats are highly saturated and have a tendency to store toxic materials from polluted feed and water. In addition, the current use of growth hormones and antibiotics, for such meat production, are generally thought to be harmful to humans. Since it usually takes several pounds of feed to produce a pound of meat, livestock production for meat is not the most efficient means of providing food for food deficient areas of the world. Multi-purpose uses of some livestock helps to overcome this latter problem.

4) Aquaculture is the commercial raising of animals and plants that live in water. In the United States, most aquaculturists raise catfish, oysters, salmon, or trout. Microalgae (algae) is a plant species grown for food, feed, vitamins, pigments, chemicals, algin paint additives, and alginates to thicken ice creams and face creams. Removal of animal feces from aquaculture pond water typically requires substantial and daily inputs of clean water that increases the cost of operation. Cold weather generally reduces production on open ponds that are frequently subject to contamination problems from dust, dirt, organic materials, insects, spiders, bird droppings, reptiles, acid rain, bacteria, and foreign algae. Greenhouse-type covers have had limited use in helping to warm ponds in winter, or to reduce contamination problems. These clear plastic canopies have required an expensive support structure for efficient operation, and the cost of such support often makes the product too expensive for the market. Mostly due to the above limitations, the aquaculture industry only produces about 6 percent of the world's annual fish catch. Overall fish supplies are believed to be declining because of the pollution of our streams, rivers, lakes, and oceans.

5) Organic Gardening is the cultivation of plants, such as fruits, vegetables, flowers, shrubs, and trees using natural or organic materials for fertilizer and pest control. This practice, which is closely related to the art and science of horticulture, was started over 40 years ago by Sir Albert Howard a British agricultural scientist. The organic movement today is gaining many supporters with the increasing scientific evidence that man could slowly be killing himself with chemical fertilizers and synthetic pesticides. The Center for Science in the Public Interest is actively promoting policies in support of organic/sustainable gardening and agriculture. Lawmakers and other state officials in Texas and Minnesota are developing policies to help assure the successful growth of organic agriculture. The chemically based agriculture of recent years is slowly being forced aside to help protect our environment.

6) Organic Water Treatment is the art and science of making polluted water clean or potable. For hundreds of years, ground seeds from the Moringa (*Moringa oleifera*) tree, applied in doses of 30 to 200 mg/liter, have been used to purify water from the Nile River in Africa. The town of Hollister, California uses microalgae ponds to facilitate removal of nutrients, heavy metals, and toxic organic materials from sewage and organic wastes. In addition, the algae generate oxygen to enhance the waste oxidation process. The New Alchemy Institute of Cape Cod, Massachusetts, founded by John Todd, has pioneered the development of an artificial marsh for organic water treatment. Wastewater is moved slowly through a hydroponic-type maize planted with bamboo, cattails, bulrushes, swamp iris/marigold, willows, and similar plants having a collective ability to take up nutrients, heavy metals, and toxic organic materials. Snails are grown in the marsh to help remove sludge. Algae may also be used as part of the system to aid water treatment as previously described. Clean and/or potable water may thus be produced by totally organic means, a means that is believed to be more economical and more protective of the environment.

BRIEF DESCRIPTION OF INVENTION

After much research and study into the various problems described in the above background, the present invention has been developed to provide a means for enhancing the organic/sustainable production of land and aquatic food, feed, and fiber plant and animal crops while reducing production costs, conserving resources, and protecting the environment. This is accomplished via a symbiotic-type polyculture supported, as needed, by organic water treatment and the means to provide optimal growth conditions year-round while also processing against contamination of crops. The invention is presented in two forms: 1) A demonstration or home production system; and 2) A commercial system for large-scale on-farm production.

The demonstration or home production system, called the Save-Earth Aquarium, consists of: 1) A small three-section quail production pen with each section having one pair of quail: 2) A 20 plus gallon aquarium tank for algae and fish production: 3) A two-section hydroponic sandbed for production of millet and vegetables; 4) A plumbing system with pump to allow recycling of water; 5) A cascade aeration ladder to provide for aeration of water as it is recycled back to the aquarium; 6) A nutrient filtration tube to facilitate filtering of quail feces placed in the aquarium: and 7) A small optional artificial marsh as may be needed for treatment of water provided to the system. For indoor use, the quail cages are placed on a table-type stand that rolls over the top of the sandbeds. Artificial lights needed for plant growth are located under this stand. Quail feces does not drop onto the stand, but is collected in a tray under the quail production pens. Tilapea is the fish of choice, and Scenedesmus is the algae of choice as hereinafter explained. The organic and symbiotic-type basis of the above system is based upon quail feces providing nutrients for the algae, algae feeding the fish, and a combination of water/fish feces/dead algae to fully sustain hydroponic crop production. Some millet is grown, in the latter, for quail feed. Any feed wasted by the quail is transferred to the aquarium for supplemental fish feed. Recycling of water is made Possible due to the fact that pond water delivered to sandbeds is biologically filtered by plants and physically filtered by sand. Once the system is operational the only water added is to replace evaporation and transpiration losses. One-half the water flow is accomplished by means of gravity so that good energy conservation is achieved. A solenoid valve with timer controls the timing and rate of water flow to sandbeds. Organic foods produced by this system include poultry meat and eggs, algae flour, fish meat, and vegetables plus cereal grains. In brief, a balanced diet free of artificial additives or chemicals is provided for home consumption. By use of the artificial marsh option, the system can also provide potable drinking water.

The commercial version of the above Save-Earth Aquarium is called the Hydroculture (hydroponic x aquaculture) Crop Production System. This latter system consists of: 1) A commercial poultry operation using organic feeds and natural/organic means of disease control; 2) A series of aquaculture ponds having special features to facilitate removal of fish feces and dead algae while also having the means to provide optimal algae and fish growth conditions on a year-round basis: 3) A series of hydro-ram pumps, plus a supplemental photovoltaic powered pump, for pumping of water with minimal energy: 4) A solenoid valve with timer and plumbing system to move pumped water to sandbeds according to a selected sequence and schedule: 5) A series of sandbeds for the hydroponic production of land crops plus filtration of pond water by biological and physical means; 6) A gravity flow system to recycle water back to ponds: 7) A cascade aeration ladder for aeration of water as it returns to ponds: 8) A filtration system to provide filtration of poultry manure effluent prior to use in ponds; 9) A special system for the selected harvesting of algae; and 10) An artificial marsh option as needed to treat water used to support the above system. Control of crop pests shall be by natural and organic means. To sustain some hydroponic land crop production during winter months, a percentage of sandbeds may have greenhouse-type canopy protection. A wide variety of crops could be produced on a commercial basis using the above hydroculture method. Any type of poultry or other livestock could be produced. A number of algae species could be selected for special algal products. Aquatic animals produced would only limited to those who feed well on algae, or animals that feed upon things feeding upon algae. The Paddlefish is an example of both feeding options since it feeds upon algae and zooplankton, and the zooplankton also feeds upon algae. Almost any land crop could be grown in the hydroponic portion of the hydroculture system. The size of the hydroponic sandbed may be adjusted upward or downward according to the density of animals produced in any hydroculture complex. A typical sandbed to water surface ratio of 8 to 1, and a sand to water volume of 4 to 1 is considered optimal for high density systems. Under normal operation, sand in the sandbeds will sustain its filtering efficiency for several years. But as organic materials accumulate, the old sand may need to be replaced with new sand.

BRIEF DESCRIPTION OF DRAWINGS

FIG. 3 is a top plan view of an aquaculture pond used in the hydroculture system of the present invention;

FIG. 4 is an enlarged sectional view of the aquaculture pond taken through line 2—2 of FIG. 3:

FIG. 5 is a top plan view of one end of the aquaculture pond showing the placement of the headhouse;

FIG. 6 is a sectional view of the pond mixing and CO2 adsorption system:

FIG. 7 is an elevational sectional view showing support balls for the pond canopy, as well as the flow divider:

FIG. 7A is an exploded sectional view of the anchor for the flow divider and support balls;

FIG. 8 is an elevational view of the light flashing affect panels on the side of the pond;

FIG. 9 is a top plan view of an aquacultural pond complex showing flow connecters for filtered effluent, as well as connecting raceways between ponds;

FIG. 10 is a schematic of the manure effluent filtration pond;

FIG. 11 is a sectional view of the hydro-ram pumping system with algae harvesting means;

FIG. 13A is a sectional view of one end of an aquaculture pond with a simulated or artificial spawning area: and FIG. 13B is a section view of the non-spawning portion of the above pond.

DETAILED DESCRIPTION OF THE INVENTION

Figure 1:
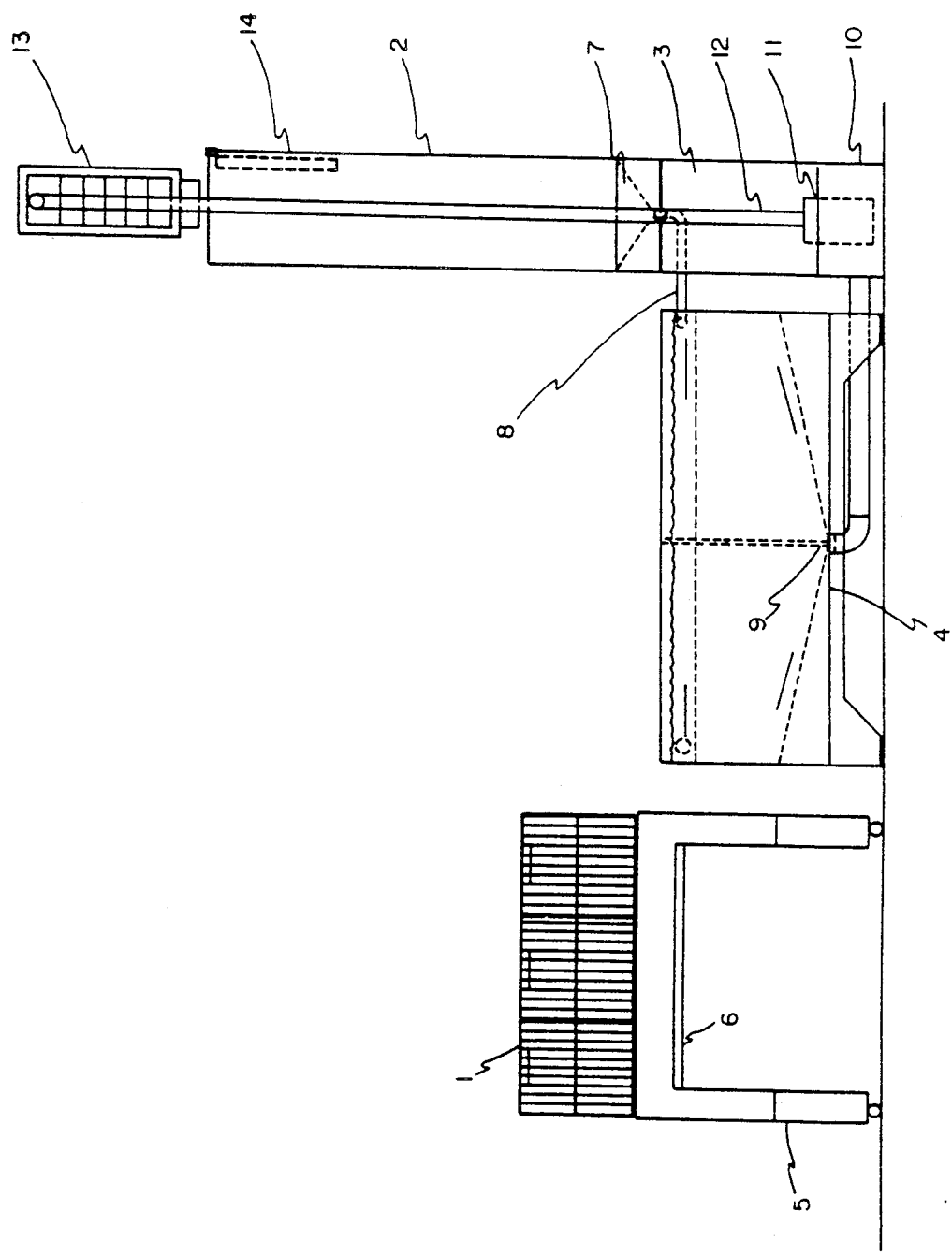
FIG. 1 is an elevational view of the Save-Earth Aquarium system of the present invention.
Figure 2:
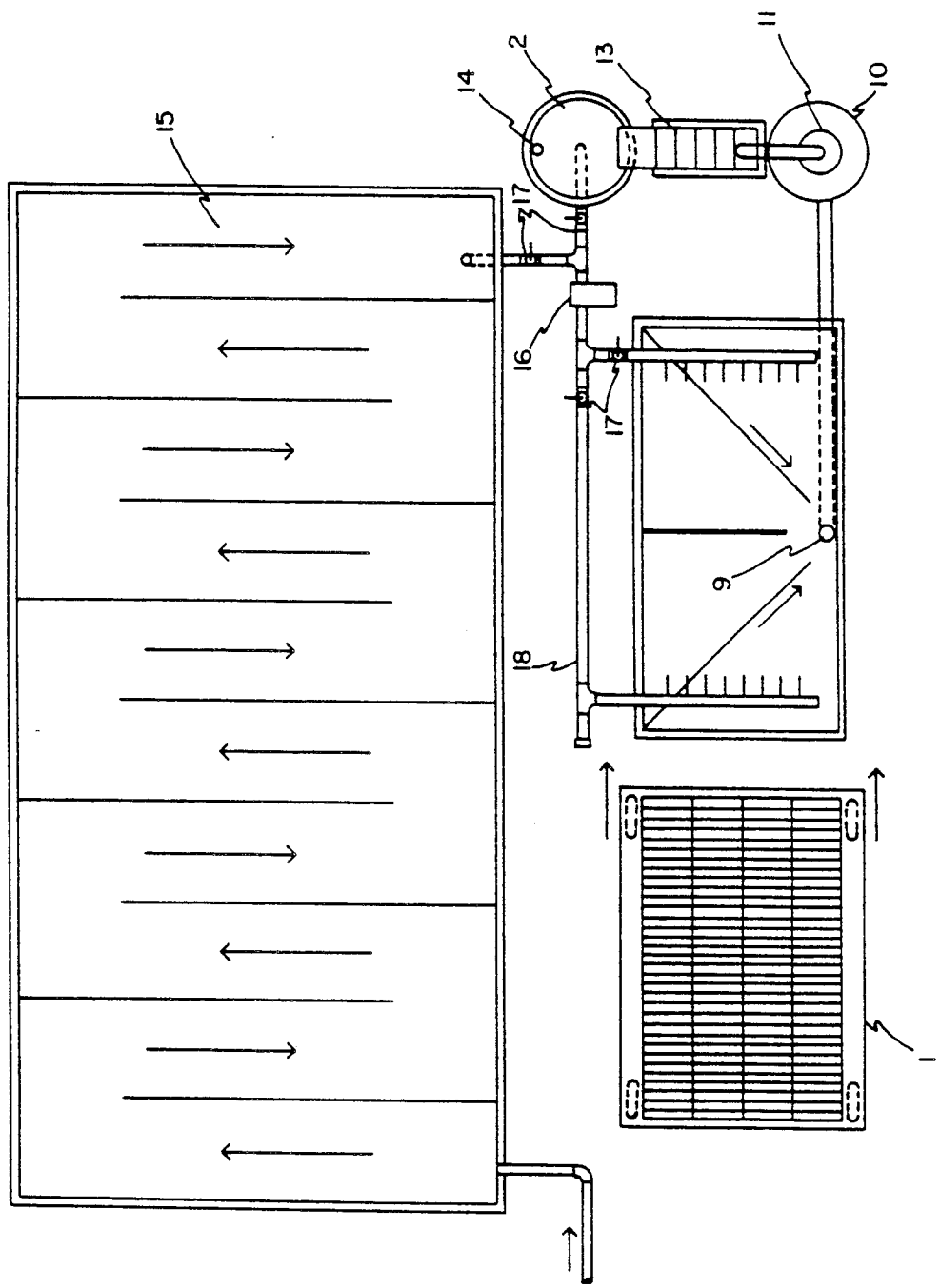
FIG. 2 is a top plan view of the Save-Earth Aquarium system showing the optional Marsh Planter.

With further reference to the drawings, the Save-Earth Aquarium is shown with its various components in FIGS. 1 and 2 including quail cages at 1, the aquarium at 2, the hydroculture planter at 4, and the marsh. planter at 15. Though suitable for a wide range of aquatic and land plant and animal crops, the embodiment described is primarily for the demonstration of organic water treatment and organic/sustainable, symbiotic-type. polyculture food & feed production methods using Cortunix (Pharoah) Quail, Red Tilapea (Sarotherodon niloticus X mossambicus) fish, Scenedesmus acutus microalgae, Pearl Millet, Red Boston Lettuce, and a decorative assortment of marsh plants.

The quail cages at 1 are a three-pen cage, 30"×24"×10" high, available from GQF Manufacturing Co. of Savannah, Georgia. Feed and water troughs are attached to the outside of pens, and a sloped floor allows eggs to roll outside of pens in a special trough. A waste tray under the pens collect feces and wasted feed. The quail pens are located on a light stand at 5 equipped with VHO artificial grow lights at 6. This stand has rollers and can be elevated so it can be easily placed over the hydroculture planter to provide lights for plants when grown indoors. Adjustments in height, for this stand, are sufficient to always keep the lights at least 1 foot above tops of plants.

An aquarium at 2 is 1 ft. in diameter by 4 ft. in height, having a capacity of 23.5 gallons, and is available from Solar Components Corp. of Manchester, New Hampshire. An aquarium drain at 7 is sloped to enhance the discharge of fish feces and dead algae at a bottom discharge around which this material settles. A solenoid valve and timer at 16 controls the frequency and amount of discharge to the hydroculture planter at 4 via plumbing system a 18 which facilitates flood irrigation of one or both sections of this planter which is filled with course sand to an average depth of 18 inches. The typical discharge flow to the hydroculture planter averages 1 gallon per hour.

Each week the feces and waste feed, collected in the quail pen tray at 1, is placed in the nutrient tube at 14 located inside the aquarium at 2. The nutrient tube filters this material, which weighs about 1 pound per week, so that solids and lost feathers remain in the tube. Nutrients from the feces are released into the water to support the growth of Scenedesmus algae which is rich in protein, vitamins, minerals, and lipids, so as to provide a complete diet for the Tilapea fish. Any waste feed, cracked millet, dissolves into the aquarium water to provide some supplemental fish feed. Using this method, 6 to 8 Tilapea can be grown until they are 2 to 3 pounds in size. At this point, hey are removed for eating or the like, and replaced with smaller Tilapea fry. One pair of Tilapea adults may be reared in a separate aquarium to provide a source of fry.

The hydroculture planter at 4 produces crops year-round by hydroponic means using discharge water from the aquarium at 2 which contains fish feces and dead algae. This combination generally contains all basic/essential macronutrients and micronutrients for most crops. Plant foliage methods for the identification of nutrient deficiencies are well known, and may be used to identify any supplemental organic nutrients that may be needed. Light and heat will be required for growth, but these can be provided by natural or artificial means. Some adjustment in pH may be required, but this can usually be accomplished by simply adding lime, and organic material. Plant diseases, harmful insects, and other plant pests can be controlled by organic means. Gurney's Seed Co. of Yankton, S. Dakota offers a good assortment of such organic products Several good organic pest control agents can be grown in the marsh planter at 15. The Neem (*Azadirachta indica*) tree is a good example. Extract from Neem tree seed have been proven effective in controlling 131 species of harmful insects Water for the aquarium is organically treated by moving water slowly through the marsh planter at 15. The maize system of this planter contains 20 gallon of water. Initially the marsh planter is filled with water which is allowed to stand for 5 days with an assortment of marsh plants having their roots dangling in the water while floating on styrofoam boards. After 5 days, 4 gallons of new water is added, and 4 gallons of process water is extracted, on a daily basis. As previously described, the marsh plants remove heavy metals and toxic materials as the water slowly moves through the marsh planter maize at 15. In 6 days the aquarium is filled by the above technique. After this time, additional water from the marsh is used for replacement of water losses from evaporation and transpiration. Some of this water may also be used as potable drinking water. The ball valves at 17 are designed so that water from the marsh planter can easily be introduced into the aquarium system.

Recycling of aquarium water is made possible by biological plant and physical sand filtration of water as it flows by gravity from the aquarium discharge to the bottom of the hydroculture planter where it drains to a collection tub at 10. A submersible pump at 11, available from W.W. Grain8er's of Chicago, Illinois or local outlets, is used to lift water to the top of a cascade aeration ladder at 13. This water absorbs oxygen from the air as it tumbles over the ladder on its way back to the aquarium. The aquarium stand at 7 elevates the aquarium to initiate gravity flow to the hydroculture planter. Slight elevation of the hydroculture planter drain at 9 allows water from this planter to gravity flow to the collection tub at 10. Use of gravity flow techniques, and the aeration ladder, generally reduces energy requirements to less than that required by a typical aquarium of similar size For remote applications, a photovoltaic panel with storage battery and electric motor can be used for pumping water.

During the start-up of the aquarium, a ½ pint jar of Scenedesmus aoutus microalgae seed stock is added to 23.5 gallons of water from the marsh planter. About 1 pound of quail feces is added to the nutrient tube at 14, with this same amount of feces being added again in 6 to 8 days. For the first two weeks, the first ball valve below the aquarium at 17 remains closed and no water is taken from the aquarium. During this period, there should be no fish in the aquarium so that the algae gets a head start. After this time, the Tilapea are added and the system operates as described above. If operated outside, the collection tub at 10 and the aeration ladder at 13 should be protected by a combination insect screen/dust cover or protective lid. Even in some indoor environments, this protective cover may be needed. The purpose of this cover is to help protect the aquarium from being contaminated by dust, dirt, insects, bird droppings, unwanted bacteria, and foreign algae. This type of action will help to sustain a uni-algal culture of Scenedesmus.

In all cases, management of the system is by organic means. Chemicals, antibiotics, growth hormones, or other artificial means are therefore avoided in the production of both plants and animals. Natural organic means are used for every aspect of the system to include disease control in livestock and aquatic animals—quail and Tilapea. As an example, extracts made from the roots of the Moringa (Moringa oleifera) tree produces a natural antibiotic substance having antimicrobial properties. The entire system, as herein described, therefore operates by natural and organic means to demonstrate this technology to organic gardeners, hobbists, students, rural villagers, and others who seek to avoid the chemical pollution of our environment while acting to provide more heathful foods for less cost and the expenditure of fewer resources.

Again with reference to the drawings, the Hydroculture Crop Production System as shown in FIGS. 4 to 13, is the commercial version of the above desired Save-Earth Aquarium. This version is capable of small to large-scale on-farm, organic/sustainable, production of all types of aquatic and land, plant and animal crops. The embodiment described in intended to demonstrate symbiotic-type, polyculture food and feed production having demonstrated the most significant yield increases while dramatically reducing production costs, conserving resources, and fully protecting the environment.

Organic production of poultry, or other livestock, is the starting point of production since animal feces/manure effluent provides a most economical source of nutrients for algae production. The type of livestock selected will depend upon the particular livestock products desired for personal use and/or marketing. To assure the organic nature of the subject invention, no growth hormones or synthetic antibiotics are used. Natural and organic means are used for pest and disease control as previously described. All feed is grown by organic means and water is treated in a marsh planted so that no heavy metals or toxic materials are transferred to the animal waste. The organic production of animals is known to those skilled in the art, and will not be herein described in any detail.

Scenedesmus acutus will again be the algae of choice for the production of aquatic animals. If algae is to be grown for a specialized crop, then some other species of algae may be selected to produce same. Several examples of possible algal products were given in the background section. Many other options are possible to include the extraction of a low saturated edible lipid (oil) from Scenedesmus and other species. Some of these oils contain bioactive metabolites having a potential anti-cancer benefit. Algae provides live food for molluscs such as oysters, clams, scallops, and mussels. In addition, algae provides live food for some fish species and zooplankters. The latter serve, in turn, as live food organisms for rearing the larvae of many freshwater and marine fish species as well as crustaceans such as prawns, shrimp, crabs, and lobsters. A great number of production options are therefore possible. For the purposes of demonstrating this invention, production of Paddlefish (*Polyodon spathula*) will be generally described. In brief, Paddlefish feed upon algae and Dahlia. The latter is a zooplankter which also feeds on algae.

In order to help prevent contamination, the aquaculture pond of this invention at 20 is covered by a greenhouse-type canopy at 32, a pond liner at 33, filtered air intake and exhaust systems ar 34 and 35, and double entry doors with clean entry foyer shown at 40 and 41. The canopy at 32 also aids in the collection of solar energy for heating of pond water during cold weather. This same canopy can also aid in cooling during hot weather, as well as modification of light transmissive characteristics as will be hereinafter explained. Floating ball canopy supports at 25 provide a roof-like shape that facilitates the protective removal of rain water, sleet, and snow while also reducing wind loads. This approach is far more economical and efficient than known methods for supporting a greenhouse-type canopy with support structures or air-inflated canopies that require joining of two layers of canopy material. A number of floating curtains, tubes, and quilts have been tried as a substitute canopy means over ponds. These floating devices tend to inhibit the natural exchange of oxygen and carbon dioxide thereby reducing the yield of many aquatic crops. Floating devices also risk causing photo-oxidative death of plants due to high oxygen tension by deterring pond outgassing. The canopy and ball support means of the present invention have demonstrated that they can overcome the problems noted above while greatly enhancing yields of aquatic crops.

By sustaining an optimal environment for algae, production of zooplankters and aquatic animals is also optimized. The detering of contamination, as described above, is most critical to maintaining a healthy uni-algal culture. Experience has shown that open ponds encourage the entry of dust, dirt, organic materials, bird droppings, rodents, reptiles, harmful bacteria, foreign algae, and a host of other yield reducing agents. Utilization of a canopy or closed means of production, however, requires additional systems for full optimization of production. These added means include: 1) Pond water circulation and upper level mixing using the paddle wheels at 22: 2) $CO_2$ mixer tubes at 23 to effectively mix lower pond levels while facilitating the absorption of $CO_2$ and air needed by aquatic crops: 3) An anchored divider curtain at 27, with bottom anchors at 28, which aids in an even flow during circulation: and 4) Round curtain end-anchors at 26 plus channel guides at 31 to prevent sedimentation as water changes direction at pond ends. The edges of the pond liner at 33, and the pond canopy at 32, are buried in a narrow trench except where they are sealed to the headhouse at 21. The headhouse allows for easy, yet contamination free, access to the pond.

The pH of ponds is adjusted with organic materials such as lime. A typical pH of 8 is desired by many aquatic plants and animals, and this is a good pH for Scenedesmus. Macronutrients, and micronutrients, are provided by manure effluent such as a mix of 10 percent poultry manure (with natural moisture) added to 90 percent well water, or other water, pre-treated in an artificial marsh to remove any toxic chemicals and/or heavy metals. This effluent is gravel and sand filtered as shown in FIGS. 9 and 10 at 48. The purpose of this filtering is to remove unwanted solids, insect eggs or larvae, and excess bacteria. For best results, the manure should be no more than 1 to 2 weeks of age, and it should be fermented in a closed tank for 7 to 10 days before filtering. Effluent amounts added to the pond are determined by nutrient demands of the algae, but the effluent added at any one time should never exceed 5 percent of the total volume of pond water. Carbon dioxide ($CO_2$) may be added as a carbon source as needed, and this can be provided by commercial $CO_2$ generators or by on-site production with $CO_2$ being metered into the pond at 30.

The present inventor's U.S. Pat. No. 4,608,175 can be modified to provide for the aerobic on-farm generation of $CO_2$ using an equal mix of manure and sawdust. Rather than just bubbling the $CO_2$ into pond water where it rapidly escapes, $CO_2$ is introduced at 24 where it passes through the $CO_2$ mixer at 23. Using a commercial $CO_2$/air diffuser, available from Aquatic Eco-Systems of Apopka, Florida, small $CO_2$ bubbles enter an auger-type mixing tube where they are given the time needed for absorption by pond water. The spiral water jet, created by this mixer, has also proven to be superior to wing-foils, propellers, and other types of pond water mixers. This supplemental mixing is needed over and above the paddle wheels because the latter does not effectively mix the pond at lower levels.

Heating of the pond at 20 is accomplished with the aid of the pond canopy at 32, using solar energy. This technology is well known to the greenhouse industry. Under most conditions, pond water will effectively store sufficient heat to keep pond water temperatures high during winter nights. If pond water temperatures become too high on a winter day, automatic controls can be used to turn on the fans at 34 and 35 to replace hot air under the canopy with cold air from outside. Again, filters are used on these fans to help prevent any contamination of the pond. No further discussion of solar heating is necessary since this is known to those skilled in the art. Water temperatures in the range of 80 to 90 degrees F. are generally the most desirable, but there will be some variation with different species. Additionally, there may need to be short-term temperature adjustments to meet spawning requirements for some aquatic animals. Most algae and zooplankters will tolerate these changes well.

To effectively deter contamination, the pond canopy at 32 must remain in place even during hot summer weather. Thus, cooling of pond water is usually required to prevent overheating. Initial cooling can be accomplished by the removal of heated air under the canopy. The fans at 34 and 35 are used for this purpose with electric power being provided by Photovoltaic panels or other means. An evaporative cooling pad can be placed in front of the intake air fan at 34, and/or pond water can be spray misted in front of this fan, to reduce air temperatures under the canopy by evaporative cooling means. Some added cooling is achieved if silver colored reflective shade screens are used over the canopy at 32 in conjunction with reducing light to desired levels. These shade screens, which can be selected for specific shading effect, are widely available to the greenhouse industry. A light level of about 800 foot candles is desirable for most aquatic plants and animals, but this level can be adjusted to meet the needs of any particular species or combination of species.

There is considerable scientific evidence suggesting that the "greenhouse effect" and destruction of the world's tropical rain forests are causing a global warming trend that is persistent and accelerating. Scientists at NASA's Goddard institute in Greenbelt, Maryland, have found that temperatures in the 1980s have been the warmest in the last 100 years. In response to the higher temperatures and increased cooling demands, the present inventor has developed an improved means of cooling whereby a silver colored reflective shade screen is slightly elevated above the canopy at 32 by means of a wire or cable support system. Water is spray misted over the top of the canopy and fans are used to exchange the air between the shade screen and canopy at a rate of one air exchange per minute. Actual use has demonstrated that air temperatures under the canopy are thus consistently reduced by more than 20 degrees F. under most circumstances.

The above wire or cable frame effectively creates a means for placement of a cover means that will facilitate modulated light photobiology using an opaque material providing alternating blackout ribs 0.8 centimeters wide and open sections 0.2 centimeters wide to simulate a light flashing effect over the pond as FIG. 8 at 44, with open sections at 46 and opaque material at 45. With the paddlewheels at 22 achieving a pond flow rate of 20 centimeters per second, an optimal dark to light flashing ratio of 40 meters per second to 10 meters per second is achieved with the light modulating cover at 44. The open sections help to prevent wind loading on this light, box-type, cover over the pond, some 6 to 8 feet in height. For a few species of algae, the flashing light effect increases production more than production is reduced by the lesser amount of total insolation A flashing light effect may or may not be desired when growing aquatic plants and animals in a polyculture pond.

To facilitate all the above operations, and to minimize any impact from diseases, pests, or contamination, the construction of large ponds is not recommended. A complex of 8 ponds each being ⅛th of a surface acre, as shown in FIG. 9, is recommended. Moreover, the pond at 20 is ideally some 3 to 4 feet deep, 184 feet in length, with a bottom width of about 24 feet, and a top width of some 30 to 32 feet with sides being sloped at 45 degrees. Some sections of the pond may be modified for special purposes such as a natural spawning area 49 for fish shown in FIG. 13A. This particular design is for the natural spawning of Paddlefish as will be hereinafter explained. The pond bottom is sloped from side to side, and end to end, with a drop of 3 inches from one side to the other, and a drop of 9 inches from one end to the other. These slopes allow dead algae and fish feces, which settle to the bottom, to move to the drain at the lowest point of the pond. The long axis of the pond should generally be oriented north and south to aid the optimal production of most aquatic crops.

Some species of bacteria occur naturally with microalgae and help to sustain the oxygen and carbon dioxide balance. A symbiotic-type relationship may exist between certain species of bacteria and algae. But the exact nature of that relationship is not fully known. Bacteria numbers will remain at the proper level so long as dead algae is not allowed to accumulate in the pond. The bacteria will collect and multiply on the dead algae and the natural balance of the pond will then begin to deteriorate. For this reason, it is important that dead algae be removed daily via the drain at 29 as hereinafter described. If zooplankters, such as Dahlia or rotifers, are to a part of the pond polyculture, they should be seeded to the pond about 2 weeks after the pond is seeded with algae. The zooplankters will generally remain healthy so long as the algae is healthy, and the health of the algae will depend upon the proper operation of the aquaculture system herein described. A part of the management system is to actually look at the algae under a microscope 2 or 3 times weakly to determine that a growing uni-algal culture is being sustained. After a period of time, the visual recognition of colors for any one algae will help in determining that algae crop is producing at a maximum rate. Seed stock for zooplankters and algae are available from a number of biological supply houses such as Carolina Biological Supply of Burlington, N. Carolina The Paddlefish (*Polyodon spathula*) uses its gill rakers to harvest algae and zooplankton from slow moving waters. This species of the Polyodontidae family can attain lengths of 6 feet and weights of 100 Pounds. The newly hatched Paddlefish fry grow some 28 inches in length, and 5 to 6 pounds in weight, in 110 days. They produce an excellent meat that is in considerable demand, therefore making the Paddlefish an excellent choice for the aquatic animal portion of this invention. The fact that ponds produce Paddlefish feed as part of the polyculture offers an extreme advantage over typical aquacultural systems requiring the purchase of commercial feeds for animals. It is current practice to engage in the expensive process of artificial induced spawning of commercial Paddlefish. This invention overcomes this problem by adding an artificial spawning area to ponds as shown in FIG. 13 at 49. The Paddlefish normally spawns in March in 10 ft. of turbid water moving over a gravel substrate at about 10,000 feet per minute. The turbid water section at 50 artificially creates these conditions using water pumps to exhaust water at 64 and intake water at 65 thereby creating the desired turbid water flow. Protective grilles at 66 prevent the fish from escaping the pond. A water baffle at 67 acts to help hold newly spawned eggs in place in the gravel substrate at 68. During the spawning period water temperature is dropped to 50 degrees F. to trigger Paddlefish spawning activity. After a two week period of spawning, water temperatures are increased to 60 degrees F. for two weeks to facilitate hatching of eggs. This one month reduction of temperatures does slow the production of algae and zooplankters, but the polyculture system remains healthy and essentially in balance.

In the recent past, plastics could not withstand prolonged exposure to UV light from the sun. Additionally, there was a lack of inexpensive food-grade plastics that would not degrade when used as a pond liner. Yet, without the use of a liner, pond water was contaminated from ground contact and water was lost by soaking into the ground. Any contamination in pond water would become more concentrated as pond water leached into the ground. Early solutions to this problem were in the form of expensive pond liners usually costing more than $1 per sq. ft. Now, however, Research Plastics of Salem, Massachusetts has developed a black 7 mil type 3,000 plastic film that effectively resists degradation by water and UV light over a period of 3 to 5 years. This plastic has been approved by the Food and Drug Administration (FDA) for direct contact with food systems, and it costs only six to eight cents per sq. ft. The inventor has successfully used this plastic on subject ponds for a period of over three years A similar type transparent plastic, made by Research Plastics, has been successfully used by the inventor for the pond canopy. In addition, this same type of plastic has been used to make the divider curtain at 27 and the inflated ball supports at 25. FDA approved plastic 55 gallon drums, available from Kerrco of Hastings, Nebraska, have been used as curtain end-anchors at 26. These drums are weighted with gravel and plug sealed so that they remain in place without floating.

The inflated ball canopy supports at 25 consist of individually inflated balls with the center two balls being 6 ft. in diameter with ball diameters being gradually reduced so that end balls are 3 ft in diameter. There is a space of 3 ft. between the outer edge of each ball. A canopy-type roof is thus formed whereby the canopy drains to both sides between balls as well as toward pond ends. All of the balls have an air line that extends to the edge of the pond to facilitate inflation as needed. On either side of a center line above the divider curtain at 27, each ball has two link-rings that are attached to eyelets in the top of this curtain. These two attachments, one on opposite sides of each ball, act to hold the balls in place while lifting the top edge of the divider curtain to the top of the pond water. Each ball is reinforced at the point of air line entry and link-ring attachment. Balls are usually made of clear transparent material, but a few balls may be made of opaque material if some shading is desired by aquatic plants or animals. There may be some advantage to having transparent ball material tinted with a red or blue color for growth enhancement of some aquatic plants and animals. More research is needed to document any actual positive benefits from such color tinting.

The pond drain at 29 is screened so as to prevent aquatic animals from being pulled into the drain pipe. By locating the drain at the lowest point of the pond, dead algae and fish feces, which settles to the bottom, will be drawn into the drain pipe along with pond water containing some live algae and zooplankters. But even with a full exchange, or recycling, of pond water every 24 hours, the loss of algae and zooplankters is minimal since they move toward the upper layers of the pond. A hydro-ram pump, or pumps, made by the Ram Company of Amherst, Virginia, will be the primary means for pumping water. The hydro-ram pump lifts water using the energy of falling water, at a rate of 10 feet of lift per 1 foot of fall. Using a poppet valve, check valve, and compression chamber the hydro-ram pumps water in a cyclic or ram pumping action created by kinetic energy of water moving through an open poppet valve. When sufficient motion is created, the poppet valve snaps shut creating a water hammer effect. A loss of pressure causes the poppet valve to reopen and the cycle is again repeated. The waste water used to create motion is collected in a basin or well having an FDA approved liner. A second hydro-ram pump could be used to aid in pumping some of the waste water so collected.

In FIG. 11, the hydro-ram pump is shown at 51 with an electric pump at 55 lifting water from the subject collection basin or well. The electric pump is powered by a PV (photovoltaic) panel at 54 for pumping water to the water tank at 57 for gravity feed irrigation to the hydroponic sandbed of this invention. A solenoid valve with timer directs selected amounts of pond water to sandbeds on a programmed schedule. Water moves by water lines shown at 56. FIG. 11 shows an intermediate catch basin at 52 with a fixed screen SWECO algae harvester at 53. This demonstrates an option to harvest algae as a separate crop. But some algae will still need to be used as a feed and fertilizer to support the full embodiment of this invention. It is possible, however, to grow and harvest algae as a sole crop using only the pond system as herein described. If this occurs, a number of other options for algae harvesting should be considered. A vibrating SWECO shaker screen is known as a good means to harvest larger species of algae such as Spirulina. For smaller species of algae, a separate settling pond should be used to concentrate algae. After concentration, an Alfa-Laval decanter centrifuge offers one of several FDA approved methods of harvesting algae for food uses. For non-food uses of algae, many other harvesting options are known to persons skilled in the art.

Figure 12:
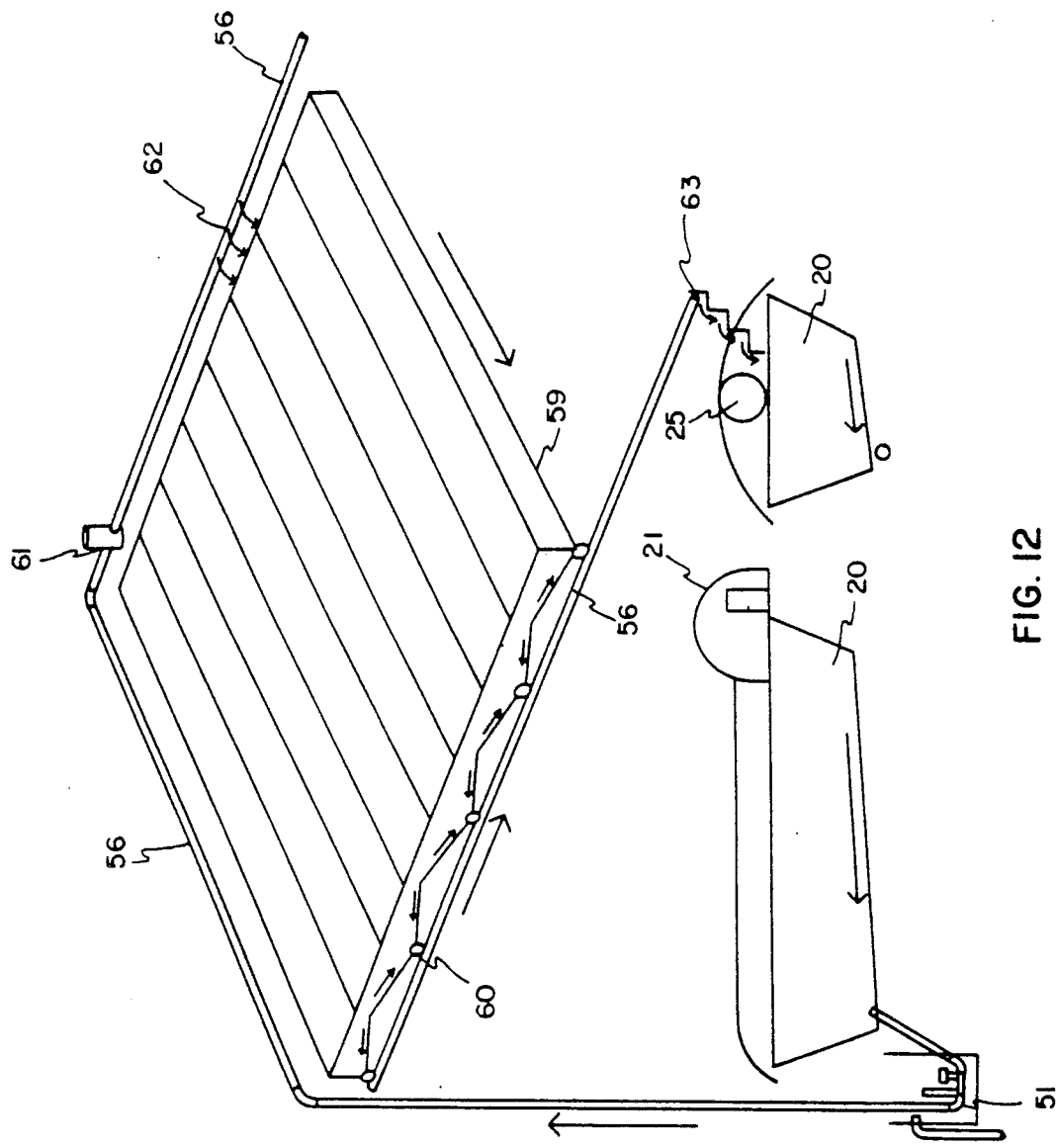
FIG. 12 is a somewhat schematic view of the hydroponic sandbeds and plumbing system of the present invention.

Water, dead algae, and fish feces from the pond of the present invention is delivered to a hydroponic sandbed one surface acre in size for each ⅛th surface acre pond. The sandbed as shown in FIG. 12, is actually divided into eight sandbeds to facilitate sequential cropping and sequential watering. This division of the sandbed also allows for ⅛th, or more, of the crop area to be under a greenhouse canopy for winter production. A sand volume of four times greater than the water volume is generally needed. Some variation will occur depending upon the size of sand and the percentage of soil or gravel contained in the sand. The above described pond water at 20 is pumped by the means shown in FIG. 11, and delivered by water lines or pipes at 56. This water may be delivered directly or indirectly by means of a water storage tank at 57. Water would be pumped from the pond at a continuous rate with the objective of exchanging and recycling 15 to 100 percent of pond water during any 24 hour period. The actual rate of exchange will depend upon the amount of dead algae and fish feces as well as requirements of the hydroponic system with associated land plants. Within the one acre hydroponic sandbed there is typically six ⅛th acre sections in various stages of crop production, and each section is flood irrigated for twenty minutes every other hour.

The design of a one acre hydroculture sandbed, for land crops produced by hydroponic means, is 208 ft.×210 ft. of actual sand having an average depth of 18 inches. This one acre unit contains 8 individual sandbeds 208 ft.×26.25 ft. Seven rows of 8 inch blocks separate the individual sandbeds so the total inside measurement is 208 ft.×214.6 ft. This area is surrounded by a rice-paddy dike and the inside bottom is sloped to facilitate water flow to the drains at 60. The entire sandbed is sloped to drain from the top to the bottom of the 208 ft. length with an overall drop of 9 inches from top to bottom. With the top of the sandbed being level, the sand depth is thus 9 inches at the upper end and 27 inches at the lower end Each individual ⅛th acre sandbed, 26.25 ft. in width, has a two inch drop from one side to the other so joining section have a common low point to allow sharing a single drain. A pond liner, identical to the one shown at 33, is placed over the sandbed structure prior to its being filled with sand. This single liner, which also covers the outer dike and divider walls, facilitates the recycling of water back to the ponds. The liner also keeps the water clean after it has been biologically filtered by plants and physically filtered by sand.

Course sand is ideal for the hydroponic system. However, the system will function with gravel, fine sand, certain sandy soils, or a combination of these. The rate of flood irrigation may require some adjustment depending upon which of these materials are used and how they actually perform in the hydroponic system. Whatever material is used as the hydroponic soil, it is usually best to screen out organic material and rocks. Additionally, sterilization of soil material will help to neutralize potential plant diseases or pests. Some sterilization techniques will also kill any weed seeds that may be in this soil material. One simple sterilization technique is to place thin layers of the soil material between layers of black plastic. A few hours of solar energy will then heat the soil material to temperatures sufficiently high to kill most disease organisms or pests. Other soil sterilization methods are known to those skilled in the art, and need not be discussed herein. Bacteria needed to aid in crop production will be introduced, to soil material in the sandbeds, along with the dead algae pumped from ponds.

A three inch hydro-ram pump will deliver about 22,000 gallons of pond water in a 24 hour period using 1 ft. of fall for each 10 ft. of lift. There are 27,154 gallons of water in one acre inch and 325,851 gallons in one acre foot of water. The ⅛th acre pond of the subject invention contains about ⅓rd acre foot of water, or 108,617 gallons. Thus, the single hydro-ram pump could move some 20 percent of the said pond water on a daily basis. In a typical operation, a second hydro-ram pump used in series would double this capacity. If a higher capacity is needed, any one pond can be equipped with a second drain to one or two additional hydro-ram pumps. These hydro-ram pumps are supplemented with photovoltaic powered electric pumps as previously explained. The solenoid valve with timer controls which sandbeds will be flood irrigated and determines the amount and frequency of water applied. By gravity flow, the water moves through the sandbed and out the sandbed drain at 60. The recycled water gravity flows down a water line to a gravity cascade aeration ladder located above the pond. This ladder aerates the water as it tumbles back into the pond. The combination of hydro-ram pumping, gravity flow recycling, and cascade aeration, provides for operation of the invention with minimal energy expenditures.

The subject invention may be operated in many different combinations as a total or partial organic/sustainable system. Many crop options are also quite possible, of which the present embodiment of the invention is but one example.

The following additional features may be added to this invention:

When using any poultry aspect of this invention indoors, the ammonia and other odors of feces may be removed by adding ¼ teaspoon per gallon of Nature Aid-B, a natural and harmless extract from the Yucca plant. This good and inexpensive product is sold by the GQF Company of Savannah, Georgia.

If an artificial marsh is used to provide potable water in Third World villages, Moringa (*Moringa oleifera*) trees should be grown to provide seeds for supplemental water purification. Moringa seedlings may be started in the hydroponic sandbeds of this invention, and then transplanted.

The effluent filtration pond shown in FIG. 10 should be designed to back-flush to facilitate removal of solids. If this is not possible, solids may be removed by flooding the pond and skimming or pumping solids off the top as they float to the surface. These solids may be used as part of an organic composting mix. Removal of solids from the filtration pond should generally be accomplished every 2 or 3 months, or more frequently as needed.

In areas where there is a limited sand supply, or in areas where organic improvement of soils would be beneficial, part of the hydroponic sandbed of this invention may be modified as explained below. One modification would be to utilize a mixture of gravel, sandy soil, and course sand to make up for a shortage of one type of sand. Another modification is the use of one or more sandbeds for organic composting to improve local soils used for land crops For the latter purpose, organic mulch, green manure, and organic fertilizers are mixed with course sand so that the sand volume is 1/10th the total. If crushed brown coal is available, this can be added at a rate of 5 percent of compost volume to increase water holding capacity. Organic pest control agents such as Neem (A. indica) seeds, should be added as needed. Some pond water, with nutrient rich algae and fish feces, is added at a rate that will keep the compost spongy but not soggy. Water drained from the compost should not be returned to ponds, but can be used to irrigate land crops. If turned every two weeks, the compost will be ready to add to soil in 3 months to increase yields.

To meet demands for potable water, this invention may be modified to purify large quantities of polluted water. If available, Moringa seed powder would be used to treat raw water. Then the water would slowly pass through an artificial marsh with a capacity equal to the quantity of water desired. The Moringa treatment and the design of the marsh are as previously described. Raw water slowly moves through the marsh for a period of 5 to 10 days so marsh plants have ample opportunity to remove toxic chemicals and heavy metals. The purification continues in an aquaculture pond of this invention dedicated to using algae for extraction of excess nutrients. This pond, or a series of algae treatment ponds, would not have aquatic animals and no effluent would be added. Algae may be harvested as a crop, but the main purpose of this algae is for the above said act of nutrient extraction. When the extraction of these nutrients is complete, pond water with algae is filtered through a hydroponic sandbed where olean sand physically filters water. Organically grown plants in this same sandbed biologically filter water. When drained from the sandbed, the water should be essentially pure and may be used for potable drinking after meeting testing requirements of local codes. The actual number of ponds or sandbeds needed will depend upon the gallons of potable water needed on a daily basis. If Moringa seeds are not available, snails should be stocked in the subject marsh to help remove any sludge.

To speed the conversion of dead algae and aquatic animal wastes to plant fertilizer/nutrients, bacteria/microorganisms of enhanced capacity may added to hydroponic sandbeds. Such enhancement is accomplished by use of the horn from a cow to bury animal feces in the ground for 3 months to provide an incubator for soil bacteria/microorganisms. After 3 months the horn is taken from the ground, and the feces/bacteria/microorganisms from the horn are then mixed into 5 gallons of water that has been organically treated. This mixture of feces, soil bacteria and microorganisms, and water are then given a static electrical charge by using an electric powered mixer that will alter the speed and direction of water movement every 10 to 15 seconds for a period of 12 to 15 minutes. The electrically charged mixture is then added to flood irrigation water at the rate of 5 gallons per $\frac{1}{8}$th acre sandbed.

To enhance the organic production of livestock, animals are fed feeds grown by the present invention. As previously discussed, insects can be controlled in production areas with the aid of Neem tree (*A. indica*) seed extracts. Additionally, a method was described for treating diseases with extracts from roots of the Moringa (*M. oleifera*) tree which contain a proven antibiotic substance. The latter is an isothiocyanate known to kill bacteria and fungi as well as having antimicrobial properties. Other organic means include various biological controls, plant derived botanical pesticides, and natural controls such as oil from the Myrrh (*Commiphora erythraea*) tree used as an insect repellant. Other options of organic pest and disease control are known to those skilled in the art, and are therefore not described herein. There are also supplemental aids for pest and disease control, aids that employ means compatible with organic production. One such example is the present inventor's natural Bird Repelling Means, U.S. Pat. No. 4,656,770.

Overall, this invention has demonstrated that any crop yield is typically 150 to 400 percent greater when crops are grown by the hydroculture method. Production costs are reduced, and resources conserved, because most production inputs are provided by this invention. The environment is fully protected by this invention because all production is by organic means. As a part of the latter benefit, this invention avoids the need to discharge aquacultural waste water with its anaerobic waste solids that release ammonia and toxic hydrogen sulfide The potable water and soil compost features are bonus benefits.

What is claimed is:

1. A method for the organic/sustainable production of land and aquatic, plants and animals, comprising: organic water treatment to remove harmful chemicals and heavy metals; a filtration means for utilizing organic nutrients in the form of animal manures; inoculation of water with selected species of microalgae which provide a balanced diet for aquatic animals to include zooplankton; a sloped water container having a bottom with drain and pumping means to move water, dead algae and aquatic animal waste to a hydroponic sandbed; a sandbed with sloped bottom and level top, to filer container water so dead algae and aquatic animal waste remains in the root zone of land plants planted in the sandbed; an organically sustained population of bacteria and other microorganisms to convert dead algae and aquatic animals wastes into organic plant fertilizer/nutrients; a plumbing system with control means to provide for the scheduled and sequential flood irrigation of sandbeds with a pre-determined amount of water; an environmental and contamination control means to sustain and enhance food/feed yields on a year-round basis despite ambient temperature fluctuations; an inflatable floating ball canopy support means to aid the environmental and contamination control means for the water container with such container being used for aquatic plant and animal production; and an organic an decontamination control means for eliminating pests and diseases in land and aquatic, plants and animals.

2. The method of claim 1 including a livestock production system based on organic feeding of animals, plus organic pest and disease control facilitating the availability of organic nutrients for microalgae production.

3. The method of claim 1 wherein microalgae is produced from the organic nutrients of claim 2, and aquatic animals are fed such algae while dead algae and aquatic animal waste, along with container water, provide the organic means for the hydroponic production of land crops.

4. The method of claim 1 wherein land crops are produced in a hydroponic sandbed with such crops being sustained by container water along with the dead algae and animal waste contained therein.

5. The method of claim 1 whereby a water pumping and aeration means, that requires minimal expenditures of energy, is provided by the combination of hydro-ram pumping, gravity flow recycling, and cascade aeration of water.

6. The method of claim 1 whereby toxic chemicals and heavy metals are organically removed from water, by use of an artificial marsh, prior to such water being used for plants or animals in the present invention.

7. The method of claim 1 whereby a thin pliable membrane flow divider curtain, with the bottom edge being anchored to the water container bottom and the top edge being attached to the floating ball support means, provides for uniform water circulation in the water container.

8. The method of claim 7 whereby container water is circulated so as to pass through a tube and auger mixing system that prevents live algae from settling on the water container bottom, while also facilitating the absorption of CO2 to enhance microalgae production system.

9. The method of claim 1 whereby the water container temperature is reduced with a reflective shade, spray misting, and air movement over the canopy to aid the environmental control operation.

10. The method of claim 9 whereby the reflective shade, or other shade, provides a cover over the water container so as to create alternating open spaces and alternating reflecting or absorbing bands that collectively provide a light flashing effect during daylight hours.

11. The method of claim 10 whereby the light absorbing or reflecting bands are four times larger than the open spaces so that a water container, with a flow rate of 20 centimeters per second, achieves an optimal light flashing ratio of 40 meters per second of dark to 10 meters per second of light.

12. The method of claim 1 whereby inflatable floating balls may be made of opaque or transparent materials as well as transparent materials having a tint of color to provide some shading or light of different pre-selected colors for growth stimulation of the aquatic plants or animals in the water container.

13. The method of claim 3 whereby container water with dead algae and aquatic animal feces is biologically filtered by plants, and physically filtered by sand so as to be returned to the water container as essentially pure water 14. The method of claim 1 whereby small-scale or hobby-type organic/sustainable production of land and aquatic, plants and animals is achieved outdoors or indoors.

15. The method of claim 6 whereby a small artificial marsh is used to provide potable water for home drinking purposes or for use in the claim 4 organic/sustainable production system.

16. The method of claim 14 whereby an aesthetic and room-scale organic/sustanable production system is used by a hobbyist, aquarium fancier, organic gardener, classroom instructor, or other person desiring.

17. The method of claim 1 whereby Moringa seed powder and marsh plants, in combination with algae and biological/physical filtration, facilitates the production of potable water.

18. The method of claim 1 whereby organic compost materials, used in increasing land crop yields, are produced with the aid of a hydroponic sandbed and container water with dead algae and aquatic animal feces.

19. The method of claim 1 whereby an artificial spawning area is created, in the water container, so as to simulate the natural spawning conditions for the aquatic animals reared therein.

20. The method of claim 4 whereby soil bacteria and other microorganisms are incubated in the earth with the aid of animal feces in a cow horn, with a static electrical charge being provided prior to these microorganisms being introduced to the hydroponic sandbeds.

* * * * *